(12) United States Patent
Omori et al.

(10) Patent No.: US 10,245,058 B2
(45) Date of Patent: Apr. 2, 2019

(54) MANIPULATOR FOR MEDICAL USE

(75) Inventors: Shigeru Omori, Ashigarakami-gun (JP); Shuichi Uenohara, Fujinomiya-shi (JP); Makoto Jinno, Ota-ku (JP); Takamitsu Sunaoshi, Yokohama (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 1348 days.

(21) Appl. No.: 11/923,159

(22) Filed: Oct. 24, 2007

(65) Prior Publication Data
US 2008/0183193 A1 Jul. 31, 2008

Related U.S. Application Data

(60) Provisional application No. 60/862,821, filed on Oct. 25, 2006.

(30) Foreign Application Priority Data

Aug. 23, 2007 (JP) .................................. 2007-216638

(51) Int. Cl.
*A61B 17/29* (2006.01)
*A61B 34/00* (2016.01)
(Continued)

(52) U.S. Cl.
CPC .............. *A61B 17/29* (2013.01); *A61B 34/70* (2016.02); *A61B 34/71* (2016.02); *A61B 34/30* (2016.02);
(Continued)

(58) Field of Classification Search
CPC ........ A61B 19/22–19/2203; A61B 2019/2207; A61B 2019/2215–2019/2238; A61B 17/29; A61B 2017/2926–2017/2944
(Continued)

(56) References Cited

U.S. PATENT DOCUMENTS 5,478,351 A * 12/1995 Meade et al. ................. 606/205
5,643,294 A * 7/1997 Tovey et al. .................. 606/148
(Continued)

FOREIGN PATENT DOCUMENTS

JP 3-213205 9/1991
JP 6-133974 5/1994

OTHER PUBLICATIONS

Extended European Search Report dated Feb. 25, 2011, in Patent Application No. 07119217.3.
(Continued)

*Primary Examiner* — Darwin P Erezo
*Assistant Examiner* — Jonathan A Hollm
(74) *Attorney, Agent, or Firm* — Whitmyer IP Group LLC

(57) ABSTRACT

A manipulator comprises a hollow shaft, wires provided on the shaft and a working unit disposed on one end of the shaft and being driven by at least one wire of the wires, the working unit having a tip tool including a rolling mechanism which rotates about an axis Or directed to a distal end thereof. A tip side surface of a proximal end member and a cover of a distal end member are relatively rotated by the rolling mechanism. The cover has a rotation identifier for indicating a degree of relative rotation of the tip side surface. The tip side surface has an alignment indicator for indicating an initial position of the cover.

20 Claims, 10 Drawing Sheets

(51) Int. Cl.
*A61B 17/00* (2006.01)
*A61B 34/30* (2016.01)
*A61B 90/00* (2016.01)

(52) U.S. Cl.
CPC .............. *A61B 2017/00455* (2013.01); *A61B 2017/2926* (2013.01); *A61B 2017/2927* (2013.01); *A61B 2034/742* (2016.02); *A61B 2090/0811* (2016.02)

(58) Field of Classification Search
USPC ................................ 606/130, 205, 170, 208
See application file for complete search history.

(56) References Cited

U.S. PATENT DOCUMENTS

| | | | | |
|---|---|---|---|---|
| 6,394,998 | B1* | 5/2002 | Wallace et al. | 606/1 |
| 6,459,926 | B1* | 10/2002 | Nowlin et al. | 600/429 |
| 6,676,684 | B1* | 1/2004 | Morley et al. | 606/205 |
| 6,913,613 | B2* | 7/2005 | Schwarz et al. | 606/206 |
| 7,261,726 | B2 | 8/2007 | Jinno et al. | |
| 2003/0100892 | A1* | 5/2003 | Morley et al. | 606/1 |
| 2004/0092912 | A1 | 5/2004 | Jinno et al. | |
| 2004/0266574 | A1* | 12/2004 | Jinno et al. | 474/153 |
| 2006/0074408 | A1 | 4/2006 | Jinno et al. | |
| 2006/0079865 | A1 | 4/2006 | Jinno et al. | |
| 2006/0079866 | A1 | 4/2006 | Jinno et al. | |
| 2006/0219065 | A1* | 10/2006 | Jinno et al. | 81/383 |
| 2007/0016174 | A1* | 1/2007 | Millman et al. | 606/1 |
| 2008/0015611 | A1 | 1/2008 | Jinno et al. | |
| 2008/0149685 | A1* | 6/2008 | Smith | A61B 17/0643 227/181.1 |

OTHER PUBLICATIONS

Japanese Office Action dated Apr. 24, 2012, in Patent Application No. 2007-216638 (with English-language translation of pertinent portions).

* cited by examiner

MANIPULATOR FOR MEDICAL USE

BACKGROUND OF THE INVENTION

Field of the Invention

The present invention relates to a manipulator for medical use, and particularly to a manipulator for medical use having a tip tool including a rolling mechanism rotatable about an axis which is directed to a distal end thereof.

Description of the Related Art

When surgery is traditionally performed, there is a long incision made so the surgeon can view and repair the internal parts of the patient. The long incision site can be a significant concern because it is subject to infection and is often the most traumatic and painful part of the patient's recovery. In recent years, many surgeons have been using endoscopic tools and performing minimally invasive surgery, thereby vastly reducing the size of the incision.

A manipulator system is composed of a manipulator body and a controller therefor, as described in Japanese Laid-Open Patent Publication No. 2004-105451, for example. The manipulator body contains an operating unit controlled by human and a working unit interchangeably removable from the operating unit.

The working unit (or an instrument) has a slender connecting shaft and an end working portion (also referred to as an end effector) disposed at the distal end of the connecting shaft. An actuator (a motor) for driving the end working portion via a wire is disposed in the operating unit. The wire is wound around a pulley in the vicinity of the proximal end. The motor in the operating unit is driven by the controller, whereby the wire is moved via the pulley.

The working unit is detachable from the operating unit, in order to easily carry out washing and the like after an operation. The working unit may be a gripper, a scissor, an electric surgical knife, an ultrasonic surgical knife, a medical drill, or the like, and may be selected depending on a procedure in a laparoscopic operation. In order to change the above working units, the working unit is preferably removable from the operating unit.

In the working unit, the pulley at the proximal end is engaged with a rotary shaft of the motor in the operating unit.

Robotic tools have been developed to further improve the minimally invasive surgical process. These tools are highly specialized. They must perform the function that a surgeon would perform in a miniaturized manner. Surgeons perform many different functions on internal organs such as cutting, scraping, and suturing.

Many of these functions require rotation of the tool in a similar manner to how the surgeon would rotate his wrist during traditional surgery. Specifically, when a tip tool has a rolling mechanism which rotates about an axis directed to a distal end thereof, a suturing operation or the like can be easily and suitably performed without the need for an operator to rotate his wrist. It is preferable that the rolling mechanism rotates in a certain rotational angular range, for example, a range of 360° or more.

The tip tool is imaged by an endoscope and displayed on a monitor. However, a gripper portion at the tip end is not necessarily imaged clearly. Also, since the gripper portion is often vertically symmetric, when the gripper portion is rotated 180°, the amount of rotation in such a gripper portion may be difficult to visually confirm.

Thus, there is a need for a device and a method for easily and reliably identifying the amount of rotation of the tool tip of a minimally invasive robotic surgical device.

SUMMARY OF THE INVENTION

One aspect of the present invention is made in view of the above problems and an object of the aspect of the present invention is to provide a manipulator for medical use, in which an operator can easily confirm a rotational angle of a rolling mechanism, even when a gripper portion at the tip end cannot be confirmed clearly by an endoscope or even when the rolling mechanism has rotated 180° or more.

A manipulator for medical use according to the aspect of the present invention comprises a hollow shaft, a power transmitting member disposed on the hollow shaft and a working unit disposed at one end of the shaft and being driven by the power transmitting member. The working unit has a tip tool including a rolling mechanism rotating around an axis directed to a distal end thereof. A proximal end member and a distal end member are relatively rotated by the rolling mechanism, and a rotation identifier is provided on at least one member of the proximal end member and the distal end member, the rotation identifier indicating a degree of rotation of another member.

According to the rotation identifier, even when a gripper portion at the tip end cannot be clearly confirmed, or even when the rolling mechanism has rotated 180° or more, an operator can easily confirm a rotational angle of the rolling mechanism.

Since an exemplary embodiment provides an instrument for identifying the degree of rotation of a tip tool, a surgeon can confirm the amount of rotation of the tip tool at each instant of time during a surgical procedure. An exemplary manipulator with a working unit for use during minimally invasive surgery is provided, which indicates the degree of rotation of a tip tool. The manipulator includes, a body, a mounting mechanism, a tip tool, and a rotation identifier. The body has a first end and a second end opposite to the first end. The mounting mechanism is mounted on the body adjacent to the second end and is capable of mounting the body to a surgical apparatus. The tip tool is mounted on the body at the first end. The rotation identifier is mounted on the body to indicate a degree of rotation of the tip tool. The axis of rotation extends from the first end of the body to the second end.

Another exemplary embodiment provides a manipulator for use during minimally invasive surgery. The manipulator includes a shaft, a working unit control mechanism, and the working unit. The working unit control mechanism is mounted on the shaft adjacent to the proximal end. The tip tool is mounted on the shaft adjacent to the distal end.

The above and other objects, features and advantages of the aspect will become more apparent from the following description when taken in conjunction with the accompanying drawings in which a preferred embodiment of the present invention is shown by way of illustrative examples.

DESCRIPTION OF THE PREFERRED EMBODIMENTS

Manipulators for medical use according to preferred embodiments of the present invention shall be described below with reference to FIGS. 1 through 10.

Figure 1:
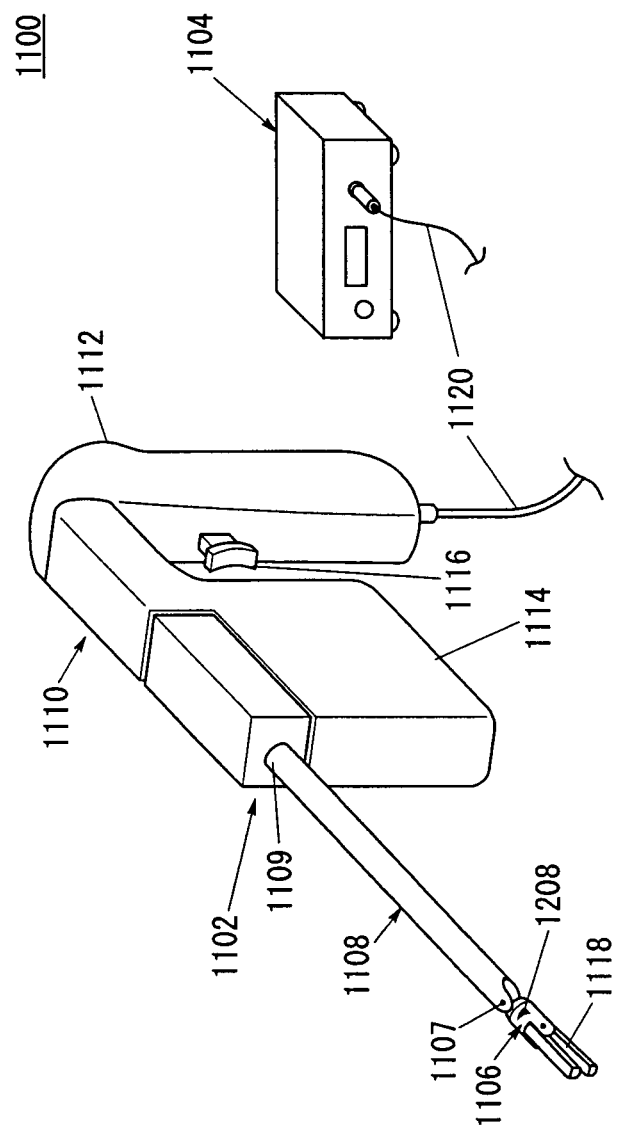
FIG. 1 is a perspective view of a manipulator in accordance with an exemplary embodiment.

With reference to FIG. 1, a perspective view of a manipulator system for medical use 1100 is shown. The manipulator system 1100 may include a manipulator 1102 and control electronics 1104. The manipulator 1102 may include a working unit (working mechanism) 1106, a hollow shaft 1108, and a working unit control mechanism 1110. The shaft 1108 has a first end 1107 and a second end 1109 opposite to the first end 1107. In general, the shaft 1108 includes an elongate tube through which control cables (power transmitting member) extend. The control cables operably couple the working unit 1106 with the working unit control mechanism 1110. The working unit 1106 mounts to the first end 1107 of the shaft 1108 using a variety of mechanisms as known to those skilled in the art both now and in the future. The working unit control mechanism 1110 mounts to the second end 1109 of the shaft 1108 using a variety of mechanisms as known to those skilled in the art both now and in the future. As used in this disclosure, the term "mount" includes join, engage, unite, connect, associate, insert, hang, hold, affix, attach, fasten, bind, paste, secure, bolt, screw, rivet, solder, weld, and other like terms.

The working unit control mechanism 1110 may be mechanical, electro-mechanical, and/or electrical as known to those skilled in the art both now and in the future. The working unit control mechanism 1110 may include a handle 1112 and a control body 1114. A surgeon maneuvers and manipulates the handle 1112 to perform minimally invasive surgical procedures using a tip tool 1118 mounted to the working unit 1106 as known to those skilled in the art both now or in the future. The handle 1112 may include a variety of control structures that may be rotated, depressed, toggled, etc. to indicate the desired movement of the tip tool 1118. For example, the handle 1112 includes a button 1116 that the surgeon may depress to cause opening and closing of the tip tool 1118.

Control electronics 1104 sends and receives electrical signals through the cable 1120 to/from the working unit control mechanism 1110. For example, control software receives electrical signals indicating movement of the button 1116, transforms the movement to appropriate signals for a mechanical system to effect movement of the tip tool 1118. The electrical signals may be analog or digital. In alternative embodiments, the manipulator system 1100 may not include control electronics 1104.

Figure 2:
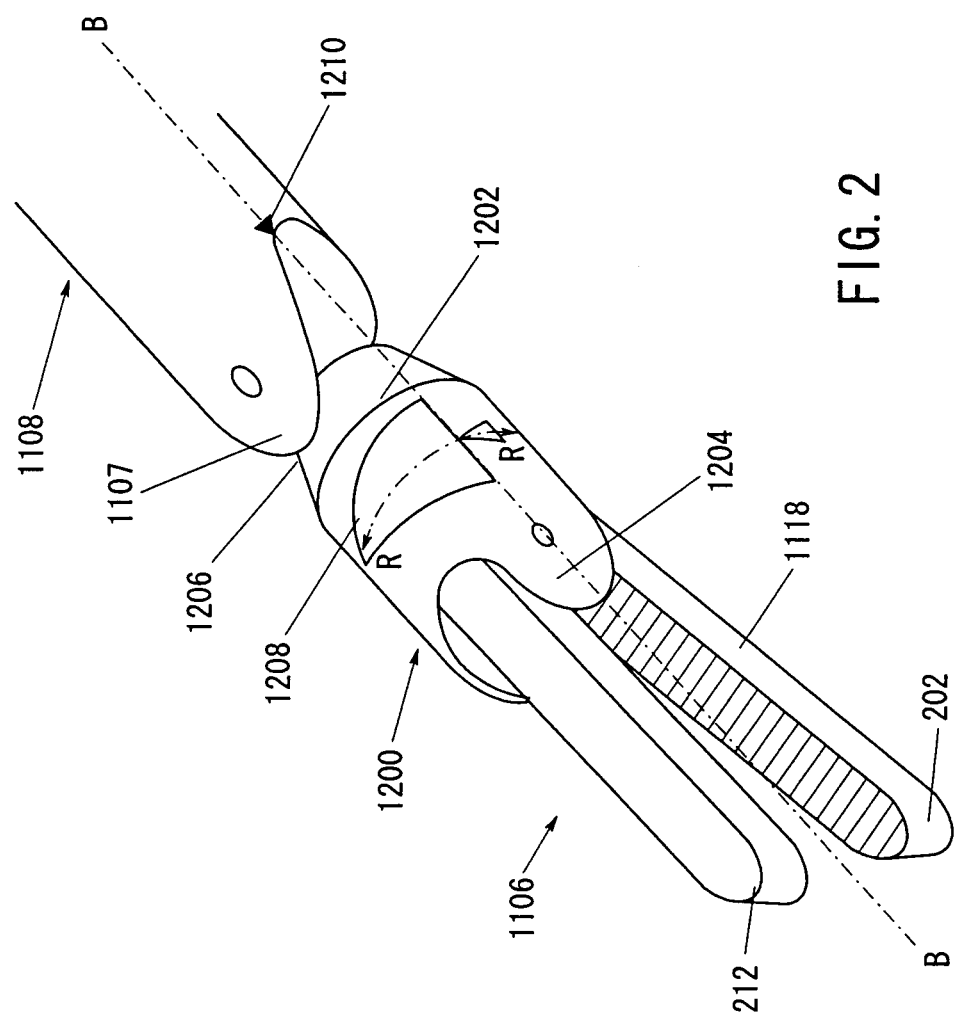
FIG. 2 is a perspective view of a working unit in accordance with the exemplary embodiment.

With reference to FIG. 2, a working unit 1106 may include a tip tool 1118, a body 1200, a mounting mechanism 1202, and a rotation identifier 1208. A proximal end member and a distal end member are relatively rotated by a rolling mechanism. The rotation identifier 1208 is disposed on at least one of the proximal end member and the distal end member, and indicates the degree of rotation of the other end member.

The body 1200 has a first end 1204 and a second end 1206 opposite to the first end 1204. The tip tool 1118 is positioned at the first end 1204 of the body 1200. The mounting mechanism 1202 is positioned at the second end 1206 of the body 1200. The working unit 1106 and/or tip tool 1118 may include many different types of devices specifically designed for cutting, scraping, suturing, grasping, etc., during a surgical procedure as known to those skilled in the art both now and in the future. As a result, the structure of the mounting mechanism 1202, used to mount the working unit 1106 to the first end 1107 of the shaft 1108, may vary as known to those skilled in the art both now and in the future.

During use of the manipulator 1102, the working unit 1106 may rotate while the shaft 1108 remains still relative to the rotation of the working unit 1106. The working unit 1106 rotates about an axis B-B that extends between the first end 1204 of the body 1200 and the second end 1206 of the body 1200 in a rotation direction R-R. In general, axis B-B also extends between the first end 1107 of the shaft 1108 and the second end 1109 of the shaft 1108. The rotation identifier 1208 indicates a degree of rotation of the tip tool 1118 and/or the working unit 1106 in the rotation direction R-R because the rotation of the tip tool 1118 and/or working unit 1106 affects how the surgeon cuts, sutures, grasps, etc. within the patient's body. The degree of rotation refers to a rotational angle with respect to a reference position.

The rotation identifier 1208 mounts to the body 1200 near the second end 1206. For example, the rotation identifier 1208 may be screened on the body 1200, molded into the body 1200, glued to the body 1200, etc. In an exemplary embodiment, the rotation identifier 1208 includes a wedge shape that the surgeon can visually see during the surgical procedure. The rotation identifier 1208 may include a plurality of wedge shapes that extend over an arc section of the body 1200. The wedge shapes may be the same or different. The angular span of the arc section may vary, for example, depending on the size of the working unit 1106. The wedge shape widens and thins as the tip tool 1118 and/or the working unit 1106 rotate in rotation direction R-R. The widening and thinning of the wedge shape visually indicates to the surgeon the degree of rotation of the tip tool 1118 and/or the working unit 1106.

The shaft 1108 may further include an alignment indicator 1210 mounted on the shaft 1108 near the first end 1107. The alignment indicator 1210 indicates an initial alignment point of the tip tool 1118 and/or the working unit 1106 with respect to the shaft 1108 to further aid the surgeon in identifying the degree of rotation of the tip tool 1118 and/or the working unit 1106 and to aid in suturing, cutting, or other surgical procedures.

Both the rotation identifier 1208 and the alignment indicator 1210 are disposed at a position closer to the proximal end than grippers 202 and 212 disposed at the distal end. Thus, even if the grippers 202 and 212 cannot be visually confirmed by an endoscope, the rotation identifier 1208 and the alignment indicator 1210 will be visually confirmed certainly.

FIG. 2 shows a structure of the working unit 1106, which will be explained in details with reference to FIGS. 3 and 4.

Figure 3:
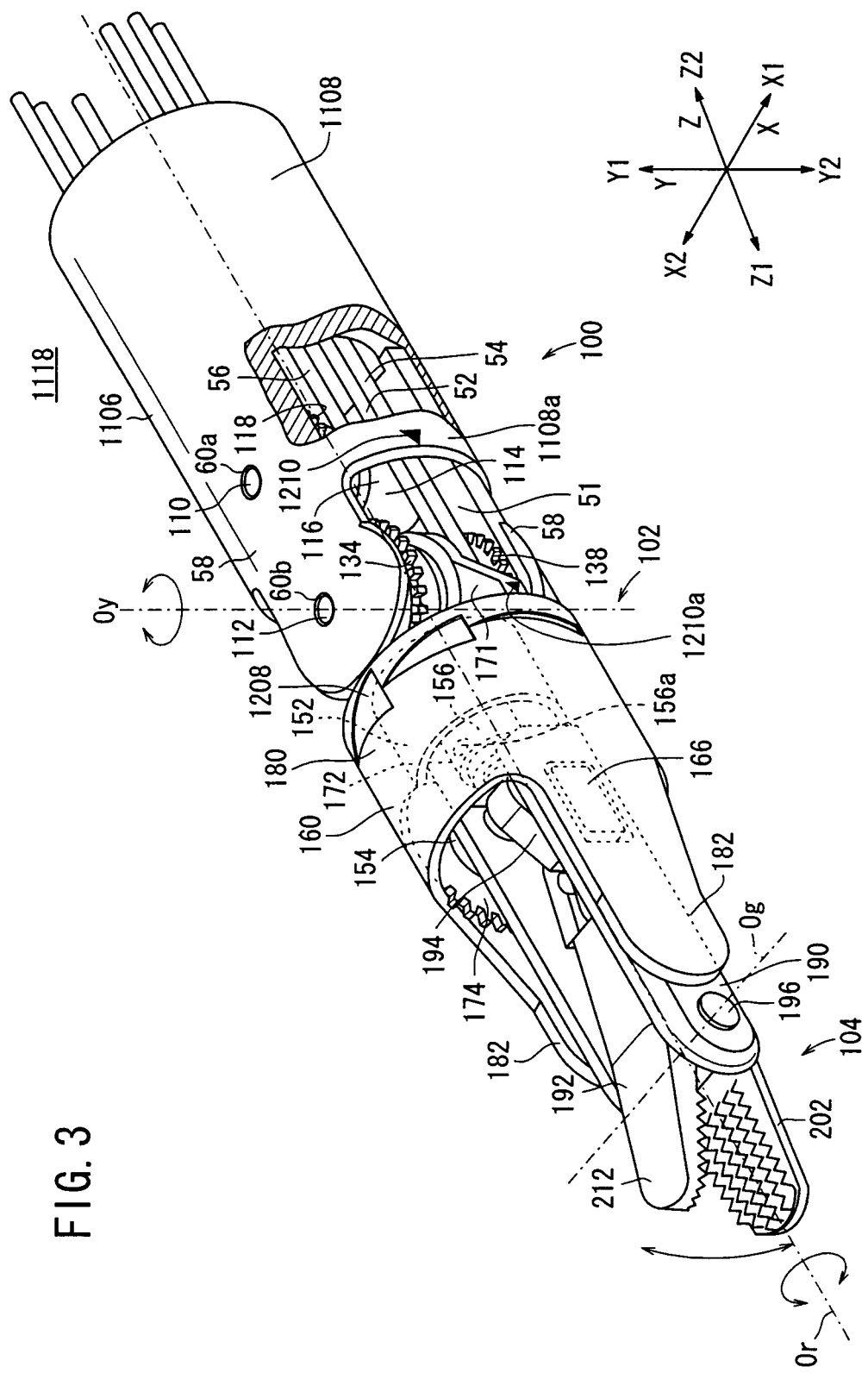
FIG. 3 is a perspective view of a working unit in the manipulator.
Figure 4:
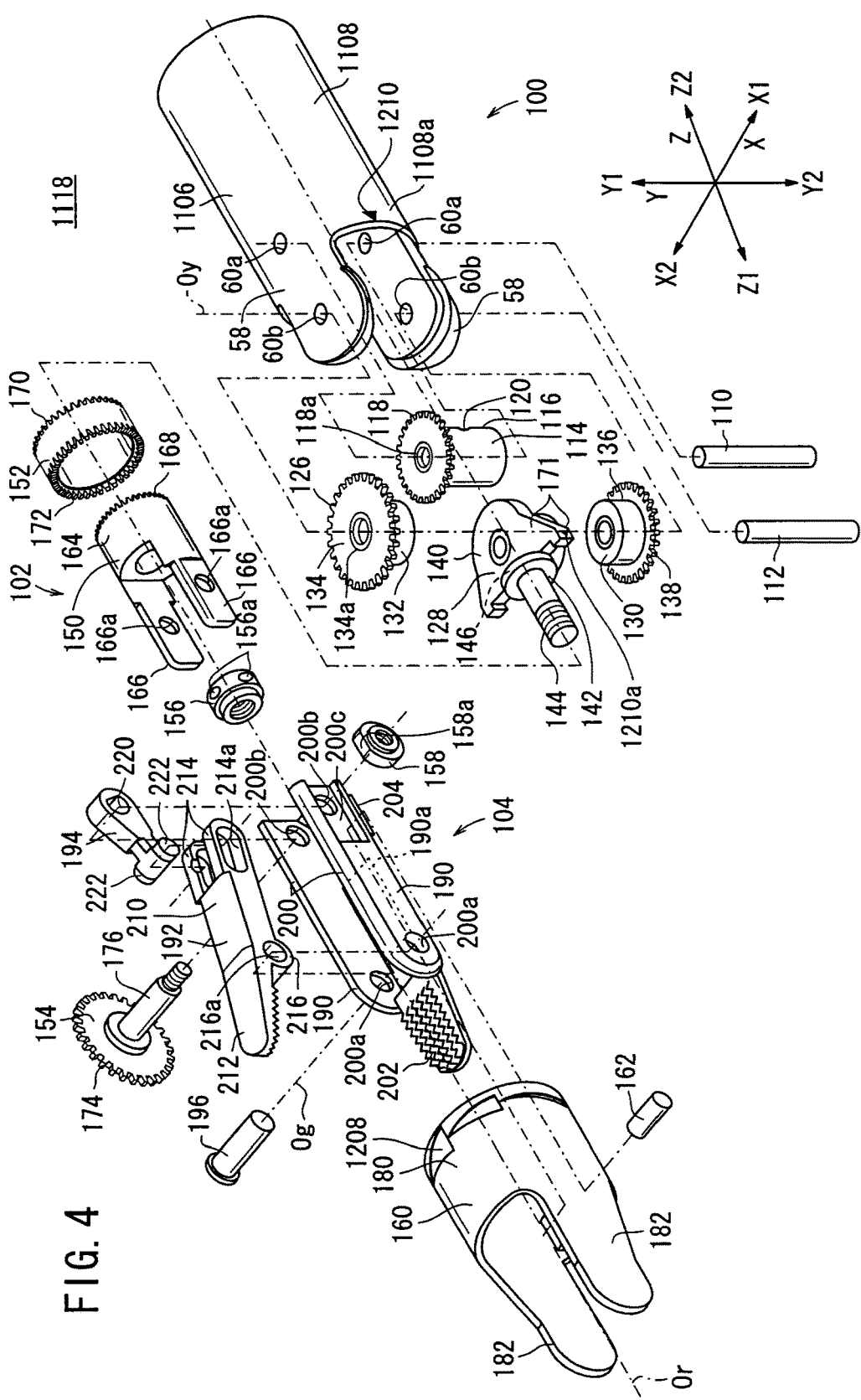
FIG. 4 is an exploded perspective view of the working unit in the manipulator.

As shown in FIG. 3, the tip tool 1118 incorporates therein mechanisms of three degrees of freedom. These mechanisms include a mechanism having a first degree of freedom for angularly moving a portion of the tip tool 1118 that is positioned ahead of a first rotational axis (pivot axis) Oy extending along the Y directions, in yawing directions about the first rotational axis Oy, a mechanism (rolling mechanism) having a second degree of freedom for angularly moving the portion of the tip tool 1118 in rolling directions about a second rotational axis Or (axis directed to the distal end), and a mechanism having a third degree of freedom for opening and closing an end effector 104 on the distal end of the tip tool 1118 about a third rotational axis Og. The second rotational axis Or is an axis which is directed to the distal end regardless of motion of the tip tool 1118 in yawing directions.

The end effector 104 serves to conduct the actual work during a surgery. For easy operation, the end effector 104 is moved through the first and second rotational axes Oy and Or. Generally, the mechanism having the third degree of freedom for opening and closing the end effector 104 is referred to as a gripper shaft, the mechanism having the first degree of freedom for angularly moving the tip tool 1118 in yawing directions as a yawing shaft, and the mechanism having the second degree of freedom for angularly moving the tip tool 1118 in rolling directions as a rolling shaft.

The tip tool 1118 comprises a wire-driven mechanism 100, a composite mechanism 102, and the end effector 104.

The wire-driven mechanism 100, the composite mechanism 102, and the end effector 104 will be described in detail below with reference to FIGS. 3 and 4.

The wire-driven mechanism 100 is disposed between the tongues 58 and serves to convert circulative movements of the respective wires 52, 54, 56 into rotational movements and transmit the rotational movements to the composite mechanism 102. The wire-driven mechanism 100 includes a shaft 110 inserted in the shaft holes 60*a*, a shaft (orthogonal shaft) 112 inserted in the shaft holes 60*b*, and a gear body 114 rotatably supported on the shaft 110. The shafts 110, 112 are press-fitted or welded securely in the shaft holes 60*a*, 60*b*. The shaft 112 is axially aligned with the first rotational axis Oy.

The gear body 114 comprises a tubular member 116 and a gear 118 disposed concentrically on an upper portion of the tubular member 116. The gear 118 is a spur gear greater in diameter than the tubular member 116. Unless otherwise specified, a gear referred to herein is a spur gear. The gear body 114 is rotatably disposed between the tongues 58. On the upper surface of the gear 118, a low annular rib 118*a* is disposed around the hole through which the shaft 110 is inserted. The annular rib 118*a* prevents the upper surface of the gear 118 from contacting the upper tongue 58, thereby reducing the sliding resistance that is imposed on the gear 118 by the upper tongue 58.

The composite mechanism 102 comprises a mechanism for opening and closing the end effector 104 and a mechanism for moving the end effector 104.

The composite mechanism 102 comprises a gear body 126, a main shaft 128, and a gear body 130, which are rotatably supported on the shaft 112 and arranged successively in the Y2 direction.

The gear body 126 comprises a tubular member 132 and a gear 134 disposed concentrically on an upper portion of the tubular member 132. The gear 134 has the same thickness as the gear 118 and is held in mesh with the gear 118. The gear 134 has a greater number of teeth than the gear 118, and hence can transmit the rotation of the gear 118 at a lower speed (with a higher torque). Alternatively, the gear 134 may be designed to transmit the rotation of the gear 118 at the same speed or a higher speed. The gear 134 has a low annular rib 134*a* disposed on the upper surface thereof around the hole through which the shaft 112 is inserted. The annular rib 134*a* prevents the upper surface of the gear 134 from contacting the upper tongue 58, thereby reducing the sliding resistance that is imposed on the gear 134 by the upper tongue 58.

The gear body 130 is essentially identical in shape to the gear body 126, but is in an upside-down orientation with respect to the gear body 126. The gear body 130 comprises a tubular member 136 and a gear 138 disposed concentrically on a lower portion of the tubular member 136. The tubular member 136 is substantially identical in diameter and shape to the tubular member 132. The gear 138 has a number of teeth which may be slightly smaller than the gear 134. The tubular member 136 is combined with a wire securing mechanism 120, which is similar to the wire securing mechanism 120 of the tubular member 116, on the side of the tubular member 136 which faces the Z2 direction, and the wire 54 is fastened to the tubular member 136 by the wire securing mechanism 120.

The main shaft 128 has a tubular member 140 through which the shaft 112 extends, an annular seat 142 coupled to the tubular member 140 and facing the Z1 direction, and a support bar 144 extending from the center of the annular seat 142 in the Z1 direction. The support bar 144 is axially aligned with the second rotational axis Or. The support bar 144 has an externally threaded distal end portion.

The annular seat 142 is slightly spaced from an outer side surface of the tubular member 140 with a protection plate 171. A hole 146 is defined between the annular seat 142 and the tubular member 140 for receiving the wire 52 to extend therethrough. The tubular member 140 is combined with a wire securing mechanism 120, which is similar to the wire securing mechanism 120 of the tubular member 116, on the side of the tubular member 140 which faces the Z2 direction, and the wire 52 is fastened to the tubular member 140 by the wire securing mechanism 120.

The protection plate 171 is in an arc shape of substantially 90° in the Z2 direction and is progressively spread in width in the Z1 direction. Stated otherwise, the plate 171 is substantially in a mountain shape in a plan view.

In response to circulative movement of the wire 52, the main shaft 128 rotates in the yawing directions about the first rotational axis Oy to cause the support bar 144 to swing in an XZ plane.

The tubular member 140, the gear body 126, and the gear body 130 are stacked together along the shaft 112 and are disposed with substantially no clearances between the tongues 58.

The composite mechanism 102 comprises a drive base 150, a gear ring 152, a geared pin 154, fastening nuts 156, 158, and a cover 160. The fastening nut 156 has a plurality of radial small holes 156*a* defined therein for inserting a narrow rotary tool. At least one of the small holes 156*a* is exposed radially (see FIG. 4). The fastening nut 158 has parallel surfaces 158*a* engageable by a rotary tool such as a wrench or the like.

The drive base 150 includes a tubular member 164 rotatably fitted over a proximal portion of the support bar 144, a pair of support arms 166 projecting in the Z1 direction from respective opposite side portions of the tubular member 164, and a face gear 168 disposed on an end face of the tubular member 164 which faces the Z2 direction. The support arms 166 serve to support the end effector 104, and have respective holes 166*a* defined therein which are lined up with each other in the X directions. After the tubular member 164 is fitted over the proximal portion of the support bar 144, the fastening nut 156 is threaded over the externally threaded distal end portion of the support bar 144, whereupon the drive base 150 is rotatably supported on the support bar 144 for rotation in the rolling directions about the axis of the support bar 144, i.e., about the second rotational axis Or.

The face gear 168 is held in mesh with the gear 138. Consequently, the drive base 150 is rotatable about the second rotational axis Or in response to rotation of the tubular member 136.

The gear ring 152 is in the form of a thin tubular member including a face gear 170 on an end face thereof facing the Z2 direction and a face gear 172 on an end face thereof facing the Z1 direction. The gear ring 152 is fitted over the tubular member 164 of the drive base 150 for sliding rotation with respect to the outer circumferential surface of the tubular member 164. The gear ring 152 is fitted over the tubular member 164 such that the face gear 170 is slightly displaced off the face gear 168 of the drive base 150 in the Z1 direction and is held in mesh with the gear 134. Since the face gear 170 is in mesh with the gear 134, the gear ring 152 is rotatable about the second rotational axis Or in response to rotation of the gear body 126.

The geared pin 154 includes a gear 174 held in mesh with the face gear 172 and a pin 176 extending in the X1 direction from the center of the gear 174. The pin 176 has an externally threaded distal end portion. The pin 176 extends through the two holes 166*a* in the support arms 166 and has its externally threaded distal end portion projecting from one of the support arms 166 which is positioned remotely from the fourth gear 174. The fastening nut 158 is threaded over the projecting externally threaded distal end portion of the pin 176. The geared pin 154, with the gear 174 held in mesh with the face gear 172, is rotatably supported by the support arms 166. The pin 176 has a D-shaped cross section for engagement with a portion of the end effector 104.

The cover 160 serves to protect the components of the composite mechanism 102 and the end effector 104, and covers the gear ring 152, the gear 174 and the like. The cover 160 includes a tube 180 extending in the Z2 direction and a pair of ears 182 projecting in the Z1 direction from respective opposite side portions of the tube 180. The ears 182 are of such a shape that circumferential wall portions of the tube 180 gradually conically extend in the Z1 direction. The cover 160 has a lower portion fastened to a portion of the end effector 104 by a cover fastening pin 162. The cover 160 has a diameter which is equal to or smaller than the shaft 1108 as viewed in front elevation.

As seen from FIG. 3, the composite mechanism 102 and the end effector 104 are elongate in the axial direction.

The cover 160 may be in the form of a hollow cylindrical or conical cover for covering the composite mechanism 102 and the end effector 104 almost in their entirety to the extent that the operation of the composite mechanism 102 and the end effector 104 will not be hampered. The cover 160 may be fastened to the end effector 104 by a pin 196.

The cover 160 of this kind prevents foreign matters (body tissues, medical agents, threads, etc.) from entering the composite mechanism 102 and the end effector 104 of the working unit.

The end effector 104 comprises a first end effector member 190, a second end effector member 192, a link 194, and a pin 196. The pin 196 is axially aligned with the third rotational axis Og.

The first end effector member 190 includes a pair of laterally spaced side walls 200 facing each other and having respective holes 200*a* defined in front end portions thereof and respective holes 200*b* defined in rear end portions thereof, a first gripper 202 projecting in the Z1 direction from lower front end portions of the side walls 200, and a cover mount 204 disposed on rear lower end portions of the side walls 200. The holes 200*a* are of such a diameter that the pin 196 can be press-fitted therein. The first gripper 202 is slightly tapered along the Z1 direction and has an arcuate distal end portion. The first gripper 202 has a number of closely spaced teeth on an entire surface thereof which faces the Y1 direction.

The front end portions of the side walls 200 are arcuate in shape. The rear end portions of the side walls 200 have respective recesses 200*c* defined in outer surfaces thereof for receiving the respective support arms 166 of the composite mechanism 102. The first end effector member 190 has a hole 190*a* (see FIG. 5) defined between the first gripper 202 and the cover mount 204 for preventing interference with the rear end portion of the second end effector member 192. The cover mount 204 has a hole defined therein for passage of the cover fastening pin 162 therethrough.

The second end effector member 192 comprises a base 210, a second gripper 212 projecting in the Z1 direction from a front end of the base 210, a pair of ears 214 extending in the Z2 direction from laterally spaced rear end portions of the base 210, and a shaft support sleeve 216 disposed on a lower surface of the front end of the base 210. The shaft support sleeve 216 has a hole 216*a* defined therein which has an inside diameter large enough to receive the pin 196 inserted therein. When the pin 196 is inserted into the shaft support sleeve 216 and press-fitted in the hole 200*a*, the second end effector member 192 is made swingable about the third rotational axis Og. The second gripper 212 is identical in shape to the first gripper 202, but is in an upside-down orientation with respect to the first gripper 202. When the second end effector member 192 is turned about the third rotational axis Og, the second gripper 212 is brought into abutment against the first gripper 202, gripping a curved needle or the like therebetween. The ears 214 have oblong holes 214*a* defined respectively therein.

The link 194 has a hole 220 defined in an end thereof and a pair of engaging fingers 222 disposed on the other end thereof and projecting laterally away from each other. The engaging fingers 222 slidably engage in the respective oblong holes 214*a*. The hole 220 is of a D-shaped cross section for receiving the pin 176 snugly therein. Therefore, the hole 220 serves to position the pin 176 and prevent the pin 176 from rotating about its own axis. When the pin 176 is inserted in the holes 166*a* and the holes 200*b*, 220 and the fastening nut 158 is threaded over the projecting externally threaded distal end portion of the pin 176, the link 194 is made swingable about the pin 176.

The rotation identifier 1208 may be disposed at an end of the cover 160 (a distal end member of the rolling mechanism) in the direction Z2, so as to be visually confirmed easily. Since the cover 160 is formed continuously and circumferentially and has an appropriate area, it is suitable to provide the rotation identifier 1208 on the cover 160. When the alignment indicator 1210 is disposed, for example, on a side surface 1108*a* of the distal end of the shaft 1108 (the proximal end member of the rolling mechanism), the alignment indicator 1210 may conveniently be always close to the rotation identifier 1208 conveniently. Since the side surface 1108*a* remains its position in a rolling direction relative to the rotation identifier 1208, even if rotating in yawing directions, it is suitable to provide the alignment indicator 1210 on the side surface 1108*a*. Specifically, the alignment indicator 1210 may preferably be provided on one of side parallel surfaces of the shaft 1108 along a second rotational axis Or of rotation along a yawing direction.

As shown by a reference number 1210a in FIG. 3, the alignment indicator may be disposed on a side surface of the protection plate 171. This position is a position where the protection plate 171 almost contacts the cover 160 and the position is not affected by a yawing action. Thus this position is suitable for the alignment indicator 1210a to indicate the rotation identifier 1208.

The rotation identifier 1208 may be provided on at least one of a proximal end member and a distal end member, which are relatively rotated by the rolling mechanism. The alignment indicator may be provided on the other end member.

Figure 5:
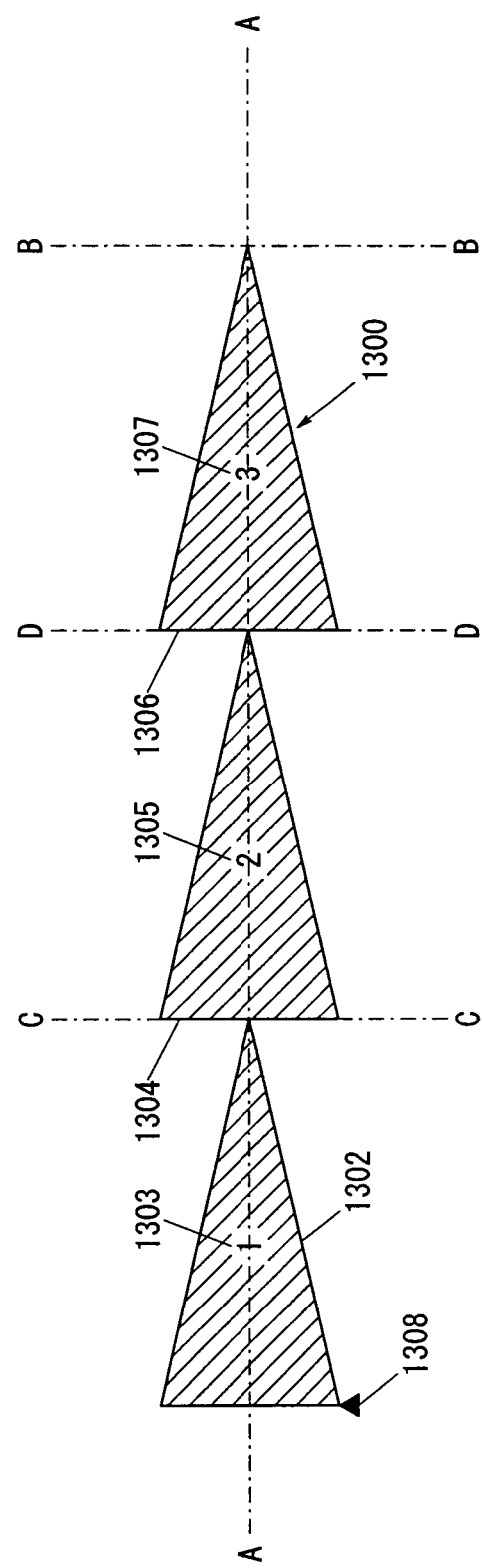
FIG. 5 is a view of a rotation identifier in accordance with a first exemplary embodiment.

With reference to FIG. 5, a rotation identifier 1208 is shown as a reference number 1300 in accordance with a first exemplary embodiment. An axis A-A extends in the direction of rotation R-R but has been unrolled to show the design of rotation identifier 1300 in its entirety. The rotation identifier 1300 includes a first isosceles triangle 1302, a second isosceles triangle 1304, a third isosceles triangle 1306, and a second alignment indicator 1308. The first isosceles triangle 1302, the second isosceles triangle 1304, and the third isosceles triangle 1306 are centered and aligned with the longer leg of the triangles oriented along the axis A-A which is in the direction of rotation R-R. An axis C-C and an axis D-D are parallel to axis B-B. Axes B-B, C-C, D-D define angular sectors of rotation identifier 1300. The first isosceles triangle 1302 extends between axis B-B and axis with C-C. The second isosceles triangle 1304 extends between axis C-C and axis with D-D. The third isosceles triangle 1306 extends between axis D-D and axis with B-B. In the exemplary embodiment of FIG. 5, the first isosceles triangle 1302, the second isosceles triangle 1304, and the third isosceles triangle 1306 extend over equal angular arc spans of 120°. In alternative embodiment, the angular arc spans may be different.

The first isosceles triangle 1302 may include a first identifier 1303. The second isosceles triangle 1304 may include a second identifier 1305. The third isosceles triangle 1306 may include a third identifier 1307. In the exemplary embodiment of FIG. 5, the first identifier 1303 is the number "1", the second identifier 1305 is the number "2", and the third identifier 1307 is the number "3". The identifiers 1303, 1305, 1307 distinguish between the triangles 1302, 1304, 1306, respectively, and further aid the surgeon in identifying the degree of rotation of the tip tool 1118 and/or the working unit 1106.

The second alignment indicator 1308 indicates an initial alignment point or zero degrees of rotation indicator with respect to the rotation identifier 1300 to further aid the surgeon in identifying the degree of rotation of the tip tool 1118 and/or the working unit 1106.

Figure 6:
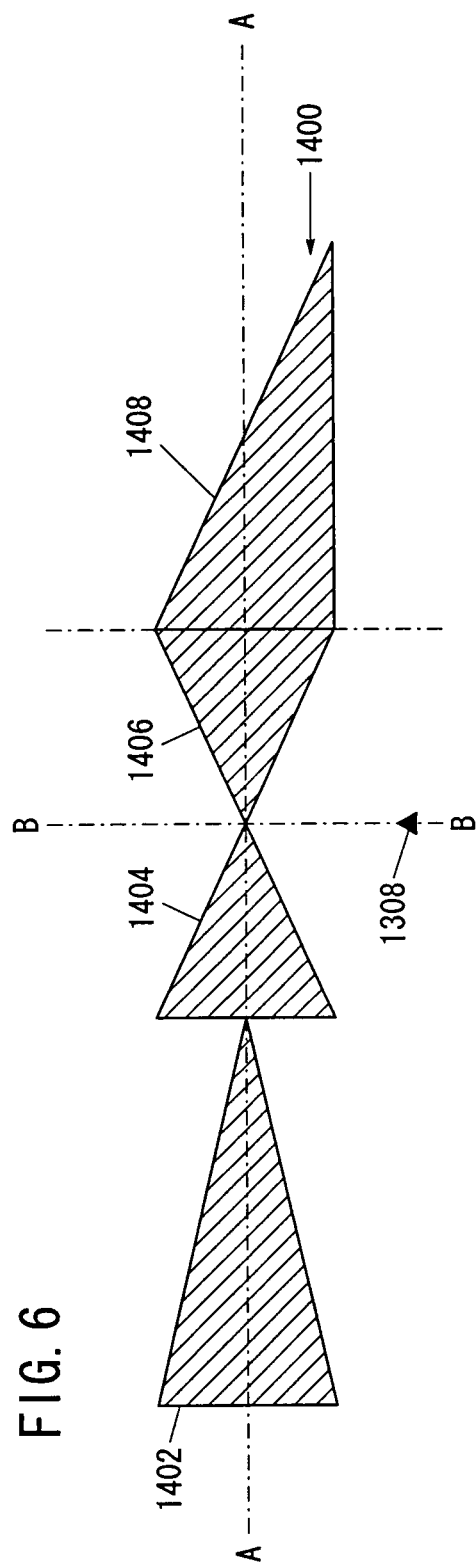
FIG. 6 is a view of a rotation identifier in accordance with a second exemplary embodiment.

With reference to FIG. 6, a rotation identifier 1208 is shown as a reference number 1400 in accordance with a second exemplary embodiment. Axis A-A extends in the direction of rotation R-R but has been unrolled to show the design of rotation identifier 1400 in its entirety. The rotation identifier 1400 includes a first isosceles triangle 1402, a second isosceles triangle 1404, a third isosceles triangle 1406, a right triangle 1408, and a second alignment indicator 1308. The first isosceles triangle 1402, the second isosceles triangle 1404, the third isosceles triangle 1406, and the right triangle 1408 are centered and aligned with the longer leg of the triangles oriented along the axis A-A which is in the direction of rotation R-R. In the exemplary embodiment of FIG. 6, the first isosceles triangle 1402 and the right triangle 1408 extend over equal angular arc spans of 120° and the second isosceles triangle 1404 and the third isosceles triangle 1406 extend over equal angular arc spans of 60°. The second isosceles triangle 1404 and the third isosceles triangle 1406 are arranged as mirror images of each other. The third isosceles triangle 1406 abuts the base of the right triangle 1408. The tip of the right triangle 1408 abuts the base of the first isosceles triangle 1402. The second alignment indicator 1308 may be aligned with axis B-B that extends between the second isosceles triangle 1404 and the third isosceles triangle 1406.

Figure 7:
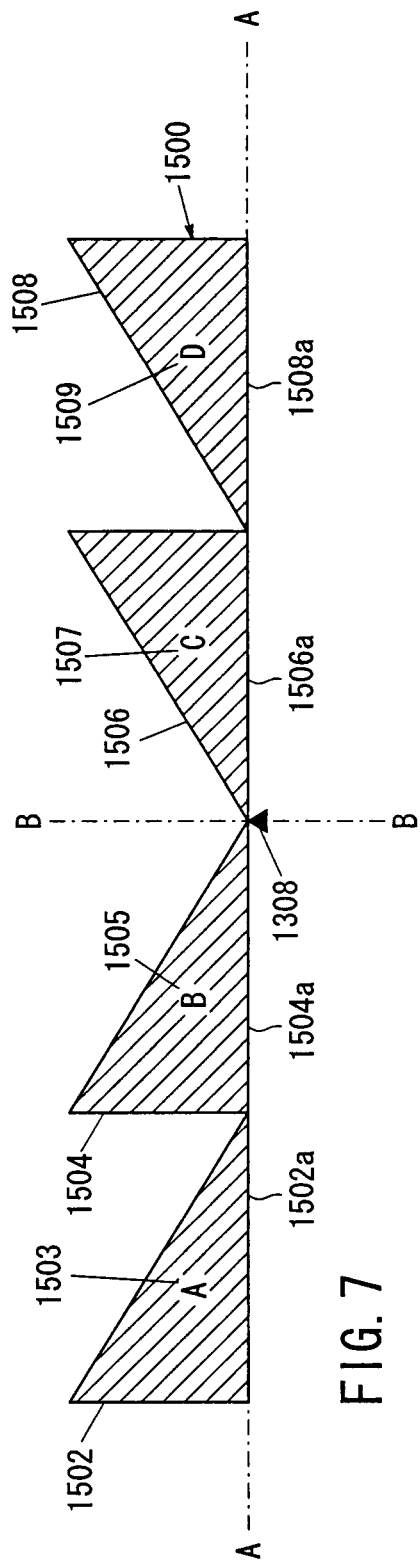
FIG. 7 is a view of a rotation identifier in accordance with a third exemplary embodiment.

With reference to FIG. 7, a rotation identifier 1500 is shown in accordance with a third exemplary embodiment. Axis A-A extends in the direction of rotation R-R but has been unrolled to show the design of rotation identifier 1500 in its entirety. The rotation identifier 1500 includes a first right triangle 1502, a second right triangle 1504, a third right triangle 1506, a fourth right triangle 1508, and second alignment indicator 1308. The first right triangle 1502, second right triangle 1504, third right triangle 1506, and fourth right triangle 1508 are aligned with the longer legs 1502a, 1504a, 1506a and 1508a of the triangles oriented along the axis A-A which is in the direction of rotation R-R. The longer leg refers to a longer side of two sides in a right angle, and is the longest side after the hypotenuse. When a side other than the shortest side is aligned with axis A-A, the direction can be easily indicated, and the width suitably does not become wider in a B-B direction uselessly. In the exemplary embodiment of FIG. 7, the first right triangle 1502, second right triangle 1504, third right triangle 1506, and fourth right triangle 1508 extend over equal angular arc spans of 90°. The second right triangle 1504 and third right triangle 1506 are arranged as mirror images of each other with the tips adjacent each other. The tip of the first right triangle 1502 abuts the base of the second right triangle 1504. The tip of the fourth right triangle 1508 abuts the base of the third right triangle 1506.

The second alignment indicator 1308 may be aligned with axis B-B that extends between the second right triangle 1504 and third right triangle 1506.

The first right triangle 1502 may include a first identifier 1503. The second right triangle 1504 may include a second identifier 1505. The third right triangle 1506 may include a third identifier 1507. The fourth right triangle 1508 may include a fourth identifier 1509. In the exemplary embodiment of FIG. 7, the first identifier 1503 is the letter "A", the second identifier 1505 is the letter "B", and the third identifier 1507 is the letter "C", and the fourth identifier 1509 is the letter "D". The identifiers 1503, 1505, 1507, 1509 distinguish between the triangles 1502, 1504, 1506, 1508, respectively, and further aid the surgeon in identifying the degree of rotation of the tip tool 1118 and/or the working unit 1106.

If a cylindrical shape like the cover 160 is viewed from the side, the cylindrical shape theoretically could be observed over a range of maximally 180°. Actually, however, the cover 160 can be visually confirmed over only a range of approximately 120°, because the body cavity 22 or the like is not sufficiently bright to observe clearly with an endoscope and edge portions of the cylindrical shape like the cover 160 are shady.

Thus, it is desirable to vary shapes of the rotation identifier on the cover 160 over a range of 120°.

For example, when one shape of shapes making up the rotation identifier is formed over a range of 120°, only the one shape can be visually confirmed in some cases and then the rotational angle cannot be determined only by the one shape. In this case, perceivable marks may be provided as a second rotation identifier. Such marks may include letters and numerals. Identifiers 1503, 1505, 1507 and 1509 as shown in FIG. 7 correspond to the second rotation identifier.

Also, in an endoscopic image, it is difficult to determine whether rotation about a rolling axis is in a plus direction or in a minus direction with respect to 0° position. In order to determine the polarity of an angle about the rolling axis, each shape (triangle) of the rotation identifier is asymmetric with respect to A-A axis in the rotation identifier 1400 in FIG. 6 and the rotation identifier 1500 in FIG. 7. Further, on the whole, the rotation identifier 1500 in FIG. 7 is symmetric with respect to 0° position (B-B axis in FIG. 7).

Thus, it is easy to obtain rotation about the rolling axis in any desired direction of a plus direction and a minus direction, even in an endoscopic image. Additionally, the polarity of a rotational position about the rolling axis, i.e., a plus direction or minus direction, can be easily determined. Also, it is easy to return back to 0° position about the rolling axis.

The rotation identifier 1400 in FIG. 6 is asymmetric also with B-B axis, thereby improving perceivability.

The rotation identifier 1208 may be formed of a variety of different shapes that are capable of visually indicating a rotation angle of the tip tool 1118 and/or the working unit 1106. A variety of triangular shapes have been shown in exemplary embodiments due to the ease of visual interpretation resulting from the linear curve formed by the leg of the triangle. Other curves suitable for indicating angular variation include arcs, steps, etc. Additionally, the curves may define different shapes such as portions of trapezoids, rectangles, hexagons, circles, etc. Additional angular spans also may be utilized in alternative embodiments. For example, nine shapes may be used with each shape/curve spanning 40°. At least two shapes generally are used so that at least one complete variation in shape is visible by the surgeon.

Figure 8:
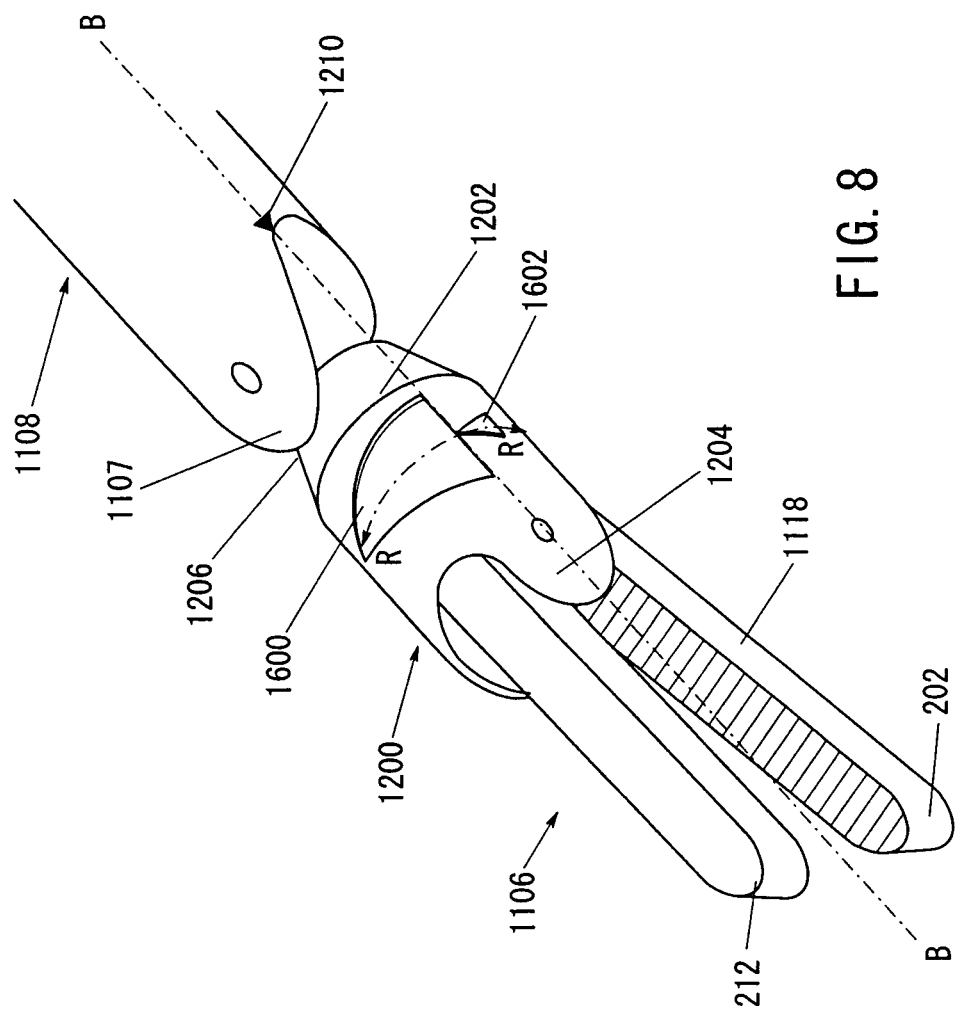
FIG. 8 is a view of a rotation identifier in accordance with a fourth exemplary embodiment.
Figure 9:
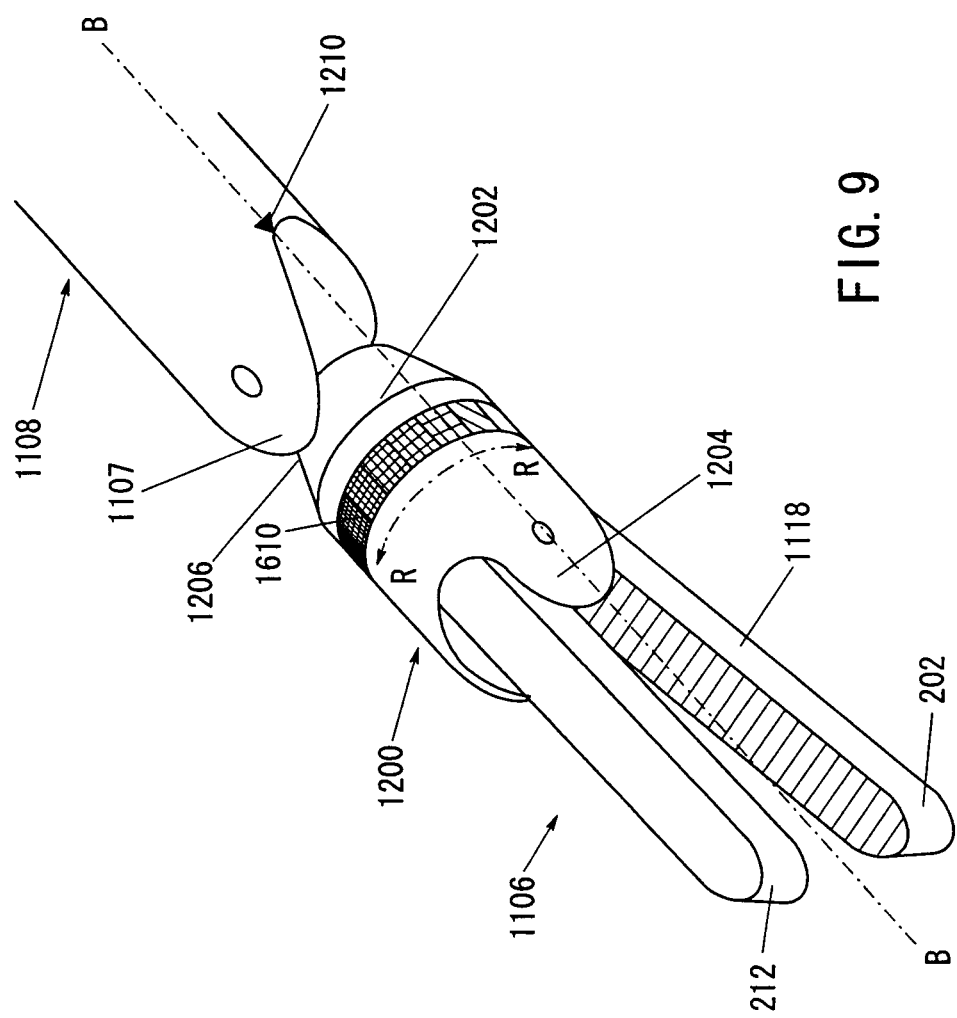
FIG. 9 is a view of a rotation identifier in accordance with a fifth exemplary embodiment.

The rotation identifier is not limited to things on the surface of the body, and may include recesses 1600 and protrusions 1602 shown in FIG. 8. The recesses 1600 or the protrusions 1602 may be formed on the circumferential surface or the end surface along the axis. The rotation identifier is not limited to the ones identified by shapes like triangles, but may be identified by colors and patterns 1610 as shown in FIG. 9. When using the colors, a rotational angle may be indicated through color gradations. Since such colors cannot be illustrated in a black and white drawing, the illustration is omitted.

According to the above manipulator for medical use, since the manipulator has a rotation identifier, an operator can easily confirm a rotational angle of the rolling mechanism visually even if grippers at the tip end cannot be obviously confirmed by an endoscope.

Also, the grippers 202 and 212 have substantially symmetric structures. Accordingly, when the rolling mechanism rotates 180°, it is difficult to determine the rotational angle even by seeing the grippers 202 and 212. However, since the manipulator has a rotation identifier, the rotational angle of the rolling mechanism can easily be confirmed visually by seeing the rotation identifier. Also, it is effective in a case where the rolling mechanism rotates 360° or more. Specifically, when the rotation identifier indicates 45°, if an operator recognizes that the rolling mechanism has been rotated 360° or more, the operator can easily recognize the current angle as being 405° (=360+45).

Figure 10:
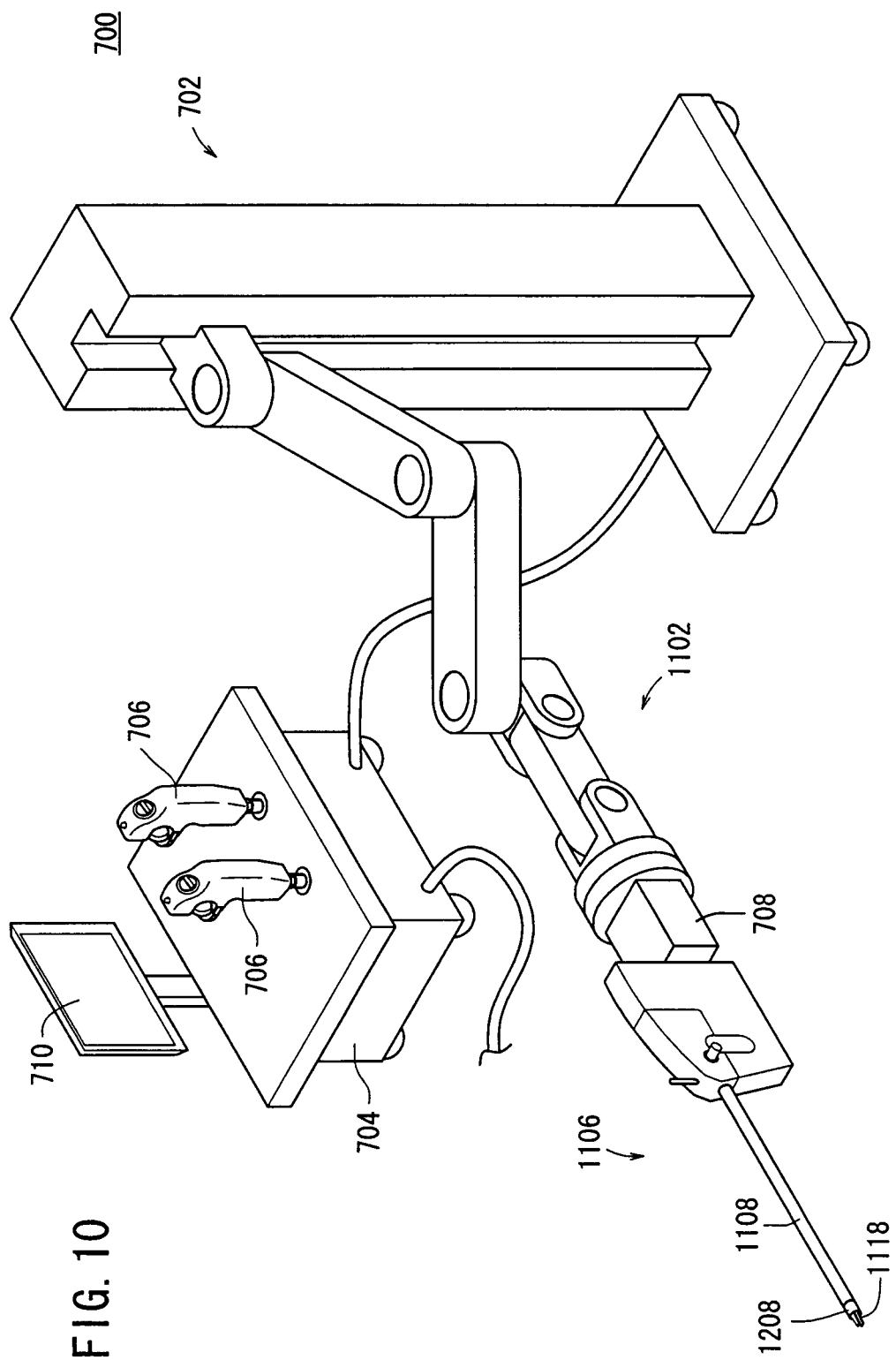
FIG. 10 is a surgical robot system in which a working unit is connected to a robotic arm at the distal end.

The above embodiments may be applied to a surgical robot system 700 as shown in FIG. 10, for example.

The surgical robotic system 700 has a multi-jointed robotic arm 702 and a console 704, and the working unit 1106 is connected to the distal end of the robotic arm 702. The robotic arm 702 has, at the distal end, the same mechanism as the above described control body 1114, whereby the working unit 1106 can be connected thereto and driven. The robotic arm 702 may be stationary type, autonomous mobile type, or the like, as long as it can move the working unit 1106. The console 704 may be table type, control panel type, or the like.

It is preferred that the robotic arm 702 has independent 6 or more joints (rotary shafts, slidable shafts, etc.), whereby the position and direction of the working unit 1106 can be optionally controlled. The distal end 708 of the robotic arm 702 is integral with a control body 1114.

The robotic arm 702 is driven under the control of the console 704, and may be driven by a program for automatic operation, by a joystick 706 disposed in the console 704, or by a combination thereof. The console 704 has a function of the above described control electronics 1104.

As described above, the rotation identifier 1208 and the alignment indicator 1210 are provided on the tip tool 1118 of the working unit 1106.

The console 704 has two joysticks 706 and a monitor 710 as an operation instructing portion. Two robotic arms 702 can be independently controlled by the two joysticks 706 though not shown. The two joysticks 706 are positioned such that they can be easily handled by both hands. Information such as an endoscopic image is shown in the monitor 710.

The joysticks 706 can be moved upward, downward, rightward, or leftward, and can be twisted or tilted. The robotic arm 702 is moved in accordance with the motion. The joystick 706 may be a master arm. A communication means between the robotic arm 702 and the console 704 may be a wired or wireless means, a network means, or a combination thereof.

While the invention has been particularly shown and described with reference to preferred embodiments, it will be understood that variations and modifications can be effected thereto by those skilled in the art without departing from the spirit and scope of the invention as defined by the appended claims.

What is claimed is:

1. A manipulator for medical use, comprising:
    a hollow shaft;
    a power transmitting member having a first wire, the power transmitting member being disposed in said shaft;
    a working unit control mechanism disposed at a first end of the shaft; and
    a working unit disposed at a second end of said shaft and being driven by said first wire, said working unit having a tip tool including a rolling mechanism rotating about a rolling axis directed to a distal end thereof;
    wherein the tip tool includes an end effector configured to grip a needle,
    wherein the first wire is fastened to a first tubular member of the rolling mechanism,
    wherein the first tubular member is rotated by the first wire to drive the rolling mechanism,
    wherein a proximal end member and a distal end member of the tip tool are relatively rotated by said rolling mechanism, and a rotation identifier is provided on at least one member of the proximal end member and the distal end member, said rotation identifier indicating a degree of rotation of the other member of the proximal end member and the distal end member, thereby indicating a degree of rotation of the tip tool with respect to the shaft, wherein said other member includes a first alignment indicator to indicate an initial position of said one member, wherein the tip tool is arranged to rotate along with the end effector in a yawing direction about a yawing axis perpendicular to the rolling axis, the tip tool being rotatable about the rolling axis at a position closer to the distal end than the yawing axis, wherein the first alignment indicator is provided on a side surface of the proximal end member, the side surface continuously connecting walls that oppose each other in a direction along which the yawing axis extends, and wherein said rotation identifier is provided on the tip tool such that, during an operation on a patient with the manipulator, the rotation identifier is positioned within a field of operation to be displayed on a monitor showing the tip tool within the patient.

2. A manipulator according to claim 1, wherein said rotation identifier comprises a triangular shape.

3. A manipulator according to claim 1, wherein said rotation identifier comprises a plurality of triangular shapes, and said triangular shapes are arranged such that sides of said triangular shapes are aligned with each other along a rolling direction of said rolling mechanism.

4. A manipulator according to claim 1, wherein said rotation identifier comprises a plurality of triangular shapes, and each of the plurality of triangular shapes defines at least one edge which abuts an adjacent at least one edge of another of the plurality of triangular shapes.

5. A manipulator according to claim 4, wherein said triangular shapes are disposed at equal intervals along a rolling direction.

6. A manipulator according to claim 4, wherein said triangular shapes are different from each other in shape.

7. A manipulator according to claim 4, wherein each of said triangular shapes has an identifiable mark.

8. A manipulator according to claim 4, wherein the at least one edge of one of the plurality of triangles is a vertex and the adjacent at least one edge of another of the plurality of triangles is a side.

9. A manipulator according to claim 1, wherein said rotational identifier comprises recesses or protrusions.

10. A manipulator according to claim 1, wherein said rotational identifier comprises colors or patterns.

11. A manipulator according to claim 1, wherein said proximal end member includes a main shaft.

12. A manipulator according to claim 1, wherein said distal end member includes a cover.

13. A manipulator according to claim 1, wherein said power transmitting member comprises the first wire extending around the first tubular member that is supported by an orthogonal shaft of the rolling mechanism, and a circulative movement of said first wire rotates the first tubular member around an axis of the orthogonal shaft such that the first tubular member and the distal end member attached to the first tubular member rotate in a plane orthogonal to the axis of the orthogonal shaft.

14. A manipulator according to claim 1, wherein said rotation identifier includes a plurality of shapes and each of the plurality of shapes of the rotation identifier has an identifiable mark to distinguish the plurality of shapes from each other.

15. A manipulator according to claim 1, wherein
said power transmitting member comprises the first wire extending around the first tubular member that includes a first gear, a second tubular member that includes a second gear, and a third tubular member, and the first tubular member, the second tubular member, and the third tubular member are supported by an orthogonal shaft of the rolling mechanism, the distal end member includes a drive base including a face gear engaged with the first gear such that a circulative movement of the first wire rotates the first gear of the first tubular member of the rolling mechanism around an axis of the orthogonal shaft, and the rotation of the first gear rotates the face gear such that the distal end rotates relative to the hollow shaft and the power transmitting member disposed in the hollow shaft in a direction around an axis of the hollow shaft, and the distal end member includes a gear ring engaged with the second gear, and a fourth gear engaged with the gear ring such that a rotation of the second gear around the orthogonal shaft rotates the gear ring around the axis of the hollow shaft, and the rotation of the gear ring around the axis of the hollow shaft rotates the fourth gear in a direction orthogonal to the hollow shaft to open and close the tip tool.

16. A manipulator according to claim 15, wherein the fourth gear is supported by a pin, and the pin is engaged with the tip tool such that, when the fourth gear is rotated, the tip tool is opened and closed.

17. A manipulator according to claim 16, wherein the pin has a D-shaped cross section.

18. A manipulator according to claim 15, wherein the gear ring is positioned radially outward from the drive base.

19. A manipulator according to claim 1, wherein said rotation identifier is formed of a plurality of shapes and a second alignment indicator, the plurality of shapes being arranged along a rolling direction of said rolling mechanism, the second alignment indicator indicating an initial position of rotation of the rotation identifier.

20. A manipulator according to claim 1, further comprising at least one additional rotation identifier, the rotation identifier and the at least one additional rotational identifier each defining at least one edge which abuts an adjacent at least one edge of the other of the rotation identifier and the at least one additional rotational identifier, wherein the rotation identifier and the at least one additional rotational identifier extend circumferentially around the distal end member.

* * * * *